(12) United States Patent
Holloway

(10) Patent No.: US 10,386,376 B2
(45) Date of Patent: Aug. 20, 2019

(54) SAMPLE CONTAINER WITH INTEGRATED TEST STRIP

(71) Applicant: JeiMei LLC, Fairfield, CT (US)

(72) Inventor: Christina Holloway, Fairfield, CT (US)

(73) Assignee: JEIMEI, LLC, Fairfield, CT (US)

( * ) Notice: Subject to any disclaimer, the term of this patent is extended or adjusted under 35 U.S.C. 154(b) by 748 days.

(21) Appl. No.: 14/936,475

(22) Filed: Nov. 9, 2015

(65) Prior Publication Data

US 2017/0131299 A1 May 11, 2017

(51) Int. Cl.
| | |
|---|---|
| *G01N 33/76* | (2006.01) |
| *G01L 3/00* | (2006.01) |
| *A61B 10/00* | (2006.01) |
| *B01L 3/00* | (2006.01) |

(52) U.S. Cl.
CPC .............. *G01N 33/76* (2013.01); *B01L 3/508* (2013.01); *A61B 10/00* (2013.01); *B01L 2200/141* (2013.01); *B01L 2300/041* (2013.01); *B01L 2300/0663* (2013.01); *B01L 2300/0832* (2013.01); *G01N 2333/59* (2013.01)

(58) Field of Classification Search
None
See application file for complete search history.

(56) References Cited

U.S. PATENT DOCUMENTS

| | | | | |
|---|---|---|---|---|
| 3,718,543 A | * | 2/1973 | Lagomarsino | ........... C12Q 1/04 435/34 |
| 4,472,353 A | * | 9/1984 | Moore | ................. G01N 31/224 422/401 |
| 4,952,373 A | | 8/1990 | Sugarman et al. | |
| 5,030,555 A | * | 7/1991 | Clemmons | ....... G01N 33/54366 422/417 |
| 5,234,813 A | * | 8/1993 | McGeehan | ....... B01L 3/502715 422/404 |
| 5,403,551 A | | 4/1995 | Galloway et al. | |
| 5,429,804 A | | 7/1995 | Sayles | |
| 5,607,863 A | | 3/1997 | Chandler | |
| 5,645,798 A | | 7/1997 | Schreiber et al. | |
| 5,976,895 A | * | 11/1999 | Cipkowski | ........... A61B 10/007 422/412 |
| 7,195,878 B2 | | 3/2007 | Cleator | |
| 7,960,132 B2 | | 6/2011 | Nakaminami et al. | |
| 8,012,762 B2 | | 9/2011 | Lee | |
| 8,202,729 B2 | | 6/2012 | Lappe et al. | |
| 8,263,019 B2 | | 9/2012 | List et al. | |
| 8,268,836 B2 | | 9/2012 | Wu | |
| 8,361,386 B2 | | 1/2013 | Davis et al. | |
| 8,927,262 B2 | | 1/2015 | Nazareth et al. | |
| 8,980,641 B2 | | 3/2015 | Clift et al. | |
| 8,992,854 B2 | | 3/2015 | Brewster et al. | |
| 9,052,311 B2 | | 6/2015 | Fallon et al. | |
| 2002/0048819 A1 | * | 4/2002 | Alley | ...................... B01L 3/502 436/169 |
| 2003/0232451 A1 | * | 12/2003 | Casterlin | .............. A61B 10/007 436/514 |
| 2007/0003115 A1 | * | 1/2007 | Patton | .................... A61B 10/00 382/128 |
| 2008/0118399 A1 | * | 5/2008 | Fleming | ............. A61B 10/0045 422/68.1 |
| 2008/0299005 A1 | * | 12/2008 | Meathrel | ................ A61K 9/006 422/552 |
| 2012/0148458 A1 | | 6/2012 | Benson | |

* cited by examiner

*Primary Examiner* — Bao Thuy L Nguyen
*Assistant Examiner* — Ellen J Marcsisin
(74) *Attorney, Agent, or Firm* — JDI Patent; Joshua D. Isenberg; Robert Pullman

(57) ABSTRACT

A test device for detection and visual identification of a specific analyte in a liquid sample such as a bodily fluid is disclosed. The device includes a collection container, a test strip affixed to an interior surface of the collection container, and a removable protective strip adhered over the test strip. The protective strip is configured to be removed from contact with the test strip after the liquid sample has been collected in order to prevent unnecessary exposure and/or contamination of the test strip. In certain embodiments, the protective strip may be removed from the contact with the test strip when the collection container is in a sealed configuration. In other embodiments, the protective strip may be dissolvable when placed in contact with the desired liquid sample. An assay specific to the anticipated analyte may be provided on the test strip.

9 Claims, 3 Drawing Sheets

SAMPLE CONTAINER WITH INTEGRATED TEST STRIP

FIELD OF THE DISCLOSURE

Aspects of the present disclosure are related to analyte testing. In particular, the present disclosure is related to maintaining the sterile nature of an analyte testing assay during the sample collection and up to the exposure process.

BACKGROUND

The field of medicine relies heavily on investigative testing performed on various compositions of biological material. Testing liquid samples, such as bodily fluids, often involves collecting a sample of a liquid and exposing the liquid to a diagnostic testing assay. An assay generally involves bringing a portion of the liquid sample into contact with an assay or test strip in order to qualitatively assess or measure the presence or amount of the functional activity of an anticipated analyte. Many such test assays or strips are known to detect for the presence of a specific chemical, hormone, or other material in liquid, such as blood, urine, or even saliva. Such tests have been designed, manufactured, produced, and marketed for use in such fields as home, industrial, veterinary, and occupational testing, among others.

A plethora of test devices are available which allow a user to test for the presence of HCG, an early indicator of pregnancy, in urine. Devices and assays have also been created for the detection of a variety of other chemicals in urine, including screenings for illegal drugs in a test subject in, for example, employment or correctional settings. These devices, to date, require that a user or test subject either urinate directly on the device or assay, or to deposit urine into a receptacle into which a testing assay or strip is placed. Unfortunately, due to the exposure of both the receptacle and the assay to the test subject, support staff, lab personnel, and even the atmosphere, contamination of the sample and/or the assay is possible even when the utmost care is observed during all steps of these testing processes. Accordingly, a need for a test device which drastically reduces the potential opportunity for contamination of an assay or test strip is needed.

It is within this context that the present disclosure arises.

BRIEF DESCRIPTION OF THE DRAWINGS

The teachings of the present disclosure can be readily understood by considering the following detailed description in conjunction with the accompanying drawings, in which.

DESCRIPTION OF THE DRAWINGS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to and without imposing limitations upon, the claimed invention.

Figure 1:
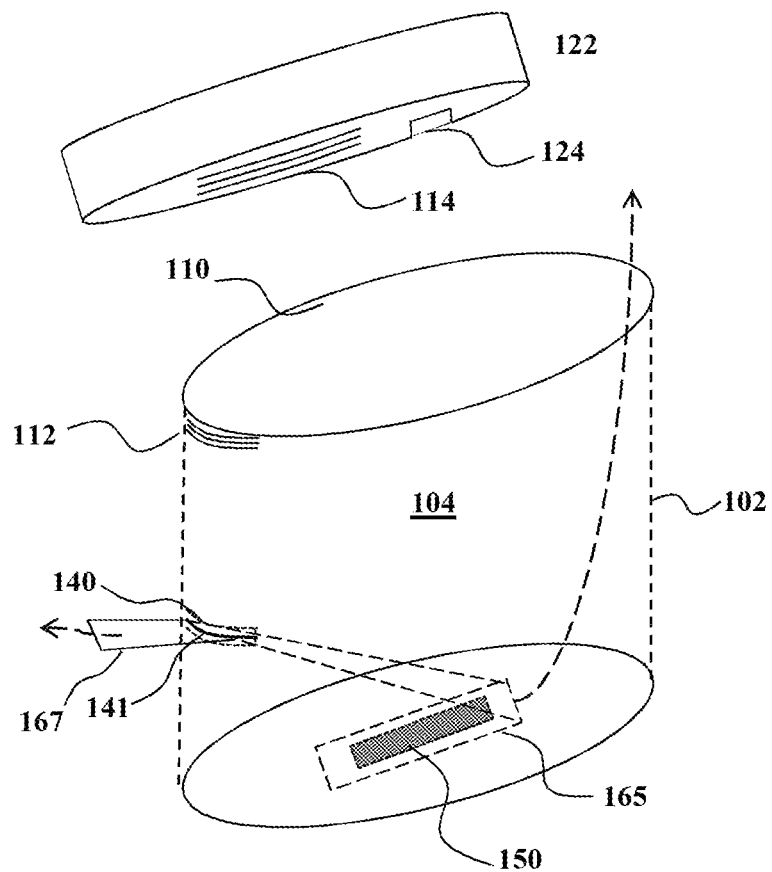
FIG. 1 is a cutaway view of a sample collection and assay analysis device in accordance with aspects of the present disclosure.

Referring now to FIG. 1 of the drawings, there is shown a test device 100 for conducting an immunoassay to detect the presence of a specific analyte in a test sample of a fluid, for example, bodily fluid. A visual indication is provided to a user or other analyst of the test sample which represents the positive or negative presence of the analyte in the test sample. A control indicator is also provided to visually assure the user or other analyst of the validity of the assay or test result. Test device 100 is capable of detecting the presence of an analyte, antigen, ligand, or other macromolecule in fluids such as bodily fluids, including but not limited to urine, blood, saliva, mucus, or perspiration. The visual indicators use a reagent which reacts to the presence of the analyte and is a conjugate of reactive color particles and/or an antibody specific to the anticipated analyte.

Device 100 is for example an antigen/receptor assay which can be used to detect the presence of an anticipated analyte in a test fluid such as urine. As provided above, such devices are used in home, industrial, veterinary, and occupational testing, among others. Generally, de ices such as these are found in home testing or clinical testing devices, for example, pregnancy detection systems, disease detection systems, or apparatus for the detection of illegal drugs. Such assays may involve an antigen/antibody reaction wherein a synthetic conjugate provides a visible tag. A specific antibody is provided specific to the antigen being detected. An absorbable indicator is provided, generally providing a simple positive/negative indicator for the presence of the antigen being detected. A control indicator is also provided to ensure the validity of the test result. Many test strips are commercially available and could be used to test for a plurality of anticipated analytes in accordance with the embodiments described herein.

Test device 100, in accordance with the present invention, is a device for collecting and analyzing a sample such as, for example, a bodily fluid. The device generally includes a container 102 having an opening 110 which provides a means for collecting the body fluid and a chamber 104 which provides a means for storing the collected body fluid. The container 102 may include screw threads 112 formed into the container proximate the opening 110 which are sized for accepting a cap 122, which may contain screw threads 114. As hereinafter described, the screw threads 114 of cap 122, when screwed onto the threads 112, provides a means for sealing the opening 110. For analysis, a typical container 102 may have a capacity of between about 100 to about 120 mL; however, the present invention is not intended to be limited to this size or capacity.

Container 102 and cap 122 may be formed, or molded, from any suitable material, such as plastic, and it will be appreciated that container 102 and cap 122 may be provided in a wide variety of shapes, e.g., as a matter of design preference or intended application. In certain embodiments of the present invention, container 102 and cap 122 are constructed of a transparent material such that the visual indications provided by a completed assay are visible through the surfaces of the container 102, even when container 102 is sealed with cap 122.

As shown in the example of FIG. 1, a test strip 150 is affixed to the bottom interior surface of container 102. In alternative embodiments, the test strip 150 may be affixed to an inside surface of the wall of container 102. Test strip 150 may be designed to test for the presence of a specific analyte, and it should be appreciated that alternative embodiments of the present invention allow for any number of analyte specific tests be performed with the device 100 of the present invention. In the present example, the test strip 150 is configured to test for the presence of Human Chorionic Gonadotropin (HCG), a hormone produced by a portion of the placenta following implantation of a blastocyst in human females during embryogenesis; the presence of this hormone in urine is an early indicator of pregnancy.

In order to avoid contamination of test strip 150, a removable protective strip 165 is secured in place over test strip 150 at the time container 102 is manufactured or when test strip 150 is affixed to container 102. Alternative embodiments provide that the test strip 150 and protective strip 165 comprise a replaceable "test panel" which can be loaded or fastened into an appropriately sterilized container 102. Protective strip 165 prevents competing analytes or other contaminants from coming into contact with test strip 150 during the time period between manufacture/assembly and use. Such contaminants include, but are not limited to microbes and other atmospheric contaminants, and contaminants present on a user or analysts skin including hormones, microbes, oils, or perspiration. Protective strip 165 may be composed of any number of materials appropriate to preventing exposure of the test strip 150 to atmospheric or other contaminants, including but not limited to plastic, metal foil, or an adhesive coating. In certain embodiments, the protective strip 165 is a coating which is dissolvable in the desired test liquid, and accordingly the protective strip 165 dissolves after a certain period of exposure to the test liquid, allowing the test strip 150 to be exposed to the test liquid. In alternative embodiments, an adhesive is applied to the area surrounding the test strip 150, and the protective strip 165 is secured in place around and over (respectively) the test strip 150, preventing the test strip 150 from being exposed to atmospheric or other contaminants.

In accordance with certain embodiments of the present invention, protective strip 165 is to be removed once the container 102 has been filled with the desired sample of test liquid. This provides that the test strip 150 is exposed only to the desired sample of test liquid, and accordingly avoids contact with the atmosphere or any other potential contaminants in order to get the most accurate potential result. In certain embodiments, the protective strip 165 can be removed by a user or other analyst who has properly donned latex gloves, or by the use of an appropriately sterile grasping device, e.g., forceps, tweezers, etc. In alternative embodiments, a portion of the protective strip 165 may extend beyond the opening 110 of container 102, and accordingly may be removed from the surface of test strip 150 without further use or waste of sterile materials. In a particular implementation, the protective strip 165 may include a free end 167 that extends to the outside of the container 102 sufficiently that a user can grasp and pull the free end 167 to remove the protective strip 165 from the test strip 150.

In alternative embodiments of the present invention, a lip 124 is provided on the cap 122 such that, when the cap 122 is fastened onto the container 102 to seal the test sample from the environment, a portion of the protective strip 165 extends past the lip of the sealed container. Such an embodiment allows for the protective strip 165 to be removed from contact with the test strip 150 even when the container 102 and the cap 122 are in a sealed configuration. In other alternative embodiments, a leak-proof seal 140 may be included on a side wall of the container 102 to allow a free end 167 of protective strip 165 to extend to the outside of the container 102. In such embodiments, the protective strip 165 may be removed from contact with the test strip 150 by pulling the protective strip through the leak-proof seal 140. Such a configuration allows for the removal of the protective strip 165 from a sealed sample environment consisting of the container 102 and the cap 122 containing a desired sample of test liquid. By way of example, and not by way of limitation, the seal 140 may be implemented with a suitable elastomer material wedged tightly into an opening the container sidewall with a slit 141 in the elastomer wide enough for the protective strip 165. In the illustrated example, the seal 140, protective strip 165, and free end 167 are configured so that the protective strip can be easily peeled back by pulling on the free end.

In embodiments of the present invention, once the protective strip 165 is removed from contact with the test strip 150, the test strip 150 will be immediately exposed to the desired sample of test liquid present in the container 102 thereby contacting the minimum potential intermediary contaminants. Once the protective strip 165 is removed, the assay configured on the test strip 150 will develop accordingly, allowing a user or other analyst to determine whether or not an anticipated analyte is present in the test liquid via the visual indicator provided by the completed assay.

Figure 2:
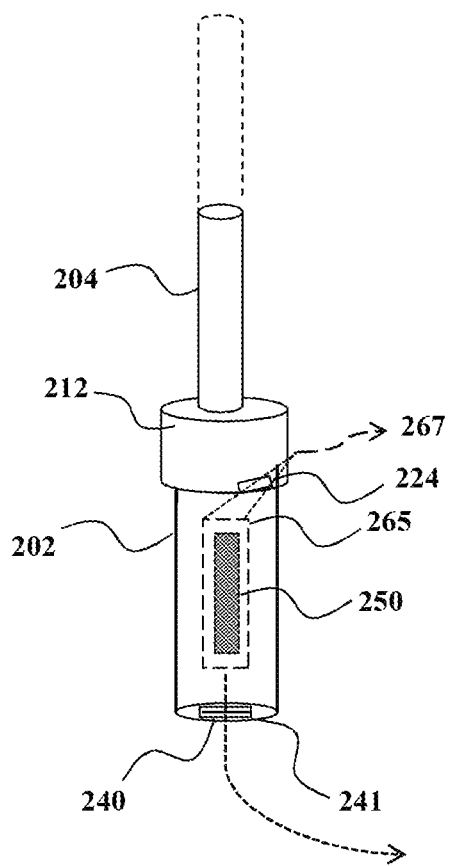
FIG. 2 is a cutaway view of a catheter-type sample collection and assay analysis device in accordance with aspects of the present disclosure.

FIG. 2 provides an alternative embodiment of the present invention wherein the test device is a container capable of being attached to a catheter. It should be appreciated that while FIG. 2 shows a standard Foley catheter for ease of recognition, alternative embodiments of the present invention allow for any number of analyte specific tests be performed in conjunction with various catheters and embodiments of the catheter testing system 200 of the present invention.

In FIG. 2, there is shown a testing system 200 for conducting an immunoassay to detect the presence of a specific analyte in a test sample of test fluid, for example, bodily fluid. A visual indication is provided to a user or other analyst of the test sample which represents the positive or negative presence of the analyte in the test sample. A control indicator is also provided to visually assure a user or other analyst of the validity of the assay or test result. The testing system 200 is capable of detecting the presence of an analyte, antigen, ligand, or other macromolecule in fluids such as bodily fluids, including but not limited to urine, blood, saliva, mucus, or perspiration. The visual indicators use a reagent which reacts to the presence of the analyte and is a conjugate of reactive color particles and/or an antibody specific to the anticipated analyte.

The system 200 may utilize, for example, an antigen/receptor assay device which can be used to detect the presence of an anticipated, analytes, in a test fluid such as urine. As provided above, such devices may be utilized in home, industrial, veterinary, and occupational testing, among others. Generally, devices such as these are found in clinical testing systems, for example, pregnancy detection systems, disease detection systems, or apparatus for the detection of illegal drugs. Such assays may involve an antigen/antibody reaction wherein a synthetic conjugate provides a visible tag. A specific antibody is provided specific to the antigen being detected. An absorbable indicator is provided, generally providing a simple positive/negative indicator for the presence of the antigen being detected. A control indicator is also provided to ensure the validity of the test result. Many test strips are commercially available and could be used to test for a plurality of anticipated analytes in accordance with the embodiments described herein.

The testing system 200 is a system for both collecting and analyzing a sample such as, for example, a bodily fluid. The system generally includes a collection container in the form of a housing 202 attached to a catheter 204. In some implementations, the housing 202 may be attached to the catheter 204 via a fastener 212. The fastener 212 may attach the housing 202 to the catheter 204 in a number of ways, e.g., screw threads, valve attachments, etc. In alternative implementations, the fastener 212 may be in the form of a cap capable of attaching to a housing 202. The cap may attach the housing 202 in a number of ways, e.g., screw threads, valve attachments, etc. For assay analysis, a typical housing 202 may have a capacity of between about 10 to about 20 mL; however, the present invention is not intended to be limited to this size or capacity. The housing 202 may be formed, or molded, from any suitable material, such as plastic, and it will be appreciated that the housing 202 may be provided in a wide variety of shapes, e.g., as a matter of design preference or intended application. In certain embodiments of the present invention, the housing 202 is constructed of a transparent material such that the visual indications provided by a completed assay are visible through the surfaces of the housing 202.

As shown in the example of FIG. 2, a test strip 250 is affixed to an interior surface of the housing 202. The test strip 250 may be designed to test for the presence of a specific analyte, and it should be appreciated that alternative embodiments of the present invention allow for any number of analyte specific tests be performed with the system 200 of the present invention. In the present example, the test strip 250 is configured to test for the presence of HCG.

In order to avoid contamination of the test strip 250, a removable protective strip 265 is secured in place over the test strip 250 at the time the housing 202 is manufactured or when the test strip 250 is affixed to the housing 202. Alternative embodiments provide that the test strip 250 and protective strip 265 comprise a replaceable "test panel" which can be loaded or fastened into an appropriately sterilized container 202. The protective strip 265 prevents competing analytes or other contaminants from coming into contact with test strip 250 during the time period between manufacture/assembly and use. Such contaminants include, but are not limited to microbes and other atmospheric contaminants, and contaminants present on a user or analysts skin including hormones, microbes, oils, or perspiration. The protective strip 265 may be composed of any number of materials appropriate to preventing exposure of the test strip 250 to atmospheric or other contaminants, including but not limited to plastic film, metal foil, or an adhesive coating. In certain embodiments, the protective strip 265 is a coating which is dissolvable in the desired test liquid, and accordingly, the protective strip 265 dissolves after a certain period of exposure to the test liquid, allowing the test strip 250 to be exposed to the test liquid. In alternative embodiments, an adhesive is applied to the area surrounding the test strip 250, and the protective strip 265 is secured in place around and over (respectively) the test strip 250, preventing the test strip 250 from being exposed to atmospheric or other contaminants.

In accordance with certain embodiments of the present invention, the nature of the mostly enclosed collection housing 202 and the system 200 allows for the protective strip 265 to be removed either before being attached to the catheter 204 or once the housing 202 has been filled/flooded with the desired sample of test liquid. This provides that the test strip 250 is exposed only to the desired sample of test liquid, and accordingly avoids contact with the atmosphere or any other potential contaminants in order to get the most accurate potential result. In certain embodiments of the present invention, a portion of the protective strip 265 extends beyond the opening of the container 202, and accordingly can be removed from the surface of the test strip 250 when a user pulls on the exposed portion of the protective strip 265. In particular implementations of the present invention, the protective strip 265 may include a free end 267 that extends to the outside of the container 202 sufficiently that a user can grasp and pull the free end 267 to remove the protective strip 265 from the test strip 250. In one such embodiment, the free end 267 of test strip 265 may extend beyond the opening of fastener 212.

In another alternative embodiment, a lip 224 is provided on the cap 212 such that, when the cap 212 is fastened onto the container 202, a free end of the protective strip 265 extends past the lid of the now-sealed container 202. Such an embodiment allows for the protective strip 265 to be removed from contact with the test strip 250 even when the container 202 and the lid 222 are in a sealed configuration.

In another alternative implementation of the present invention, a leak-proof seal 240 may be included on the housing 202 to allow a portion of the protective strip 265 to extend externally from housing 202. In such embodiments, the protective strip 265 may be removed from contact with test strip 250 by pulling a free end of the protective strip through a slit 241 in the leak-proof seal 240. Such a configuration allows for the removal of the protective strip 265 from a sealed sample environment consisting of the catheter system 200 of the catheter 204 attached to the collection housing 202, which is able to contain a desired sample of test liquid as produced by a patient. By way of example, and not by way of limitation, the seal 240 may be implemented with a suitable elastomer material wedged tightly into an opening the container sidewall with a slit in the elastomer wide enough for the protective strip 265. The seal 240 and protective strip 265 may be configured so that the protective strip can be easily peeled back by pulling on, a free end of the protective strip that passes through the slit to the outside of the container.

In embodiments of the present invention, once the protective strip 265 is removed from contact with the test strip 250, the test strip 250 will be exposed to the desired sample of test liquid present in the housing 202, either immediately or as the patient produces the desired sample, thereby contacting the minimum potential intermediary contaminants. Once the protective strip 265 is removed, the assay configured on the test strip 250 will develop accordingly, allowing a user or other analyst to determine whether or not an anticipated analyte is present in the test liquid via the visual indicator provided by the completed assay.

Figure 3:
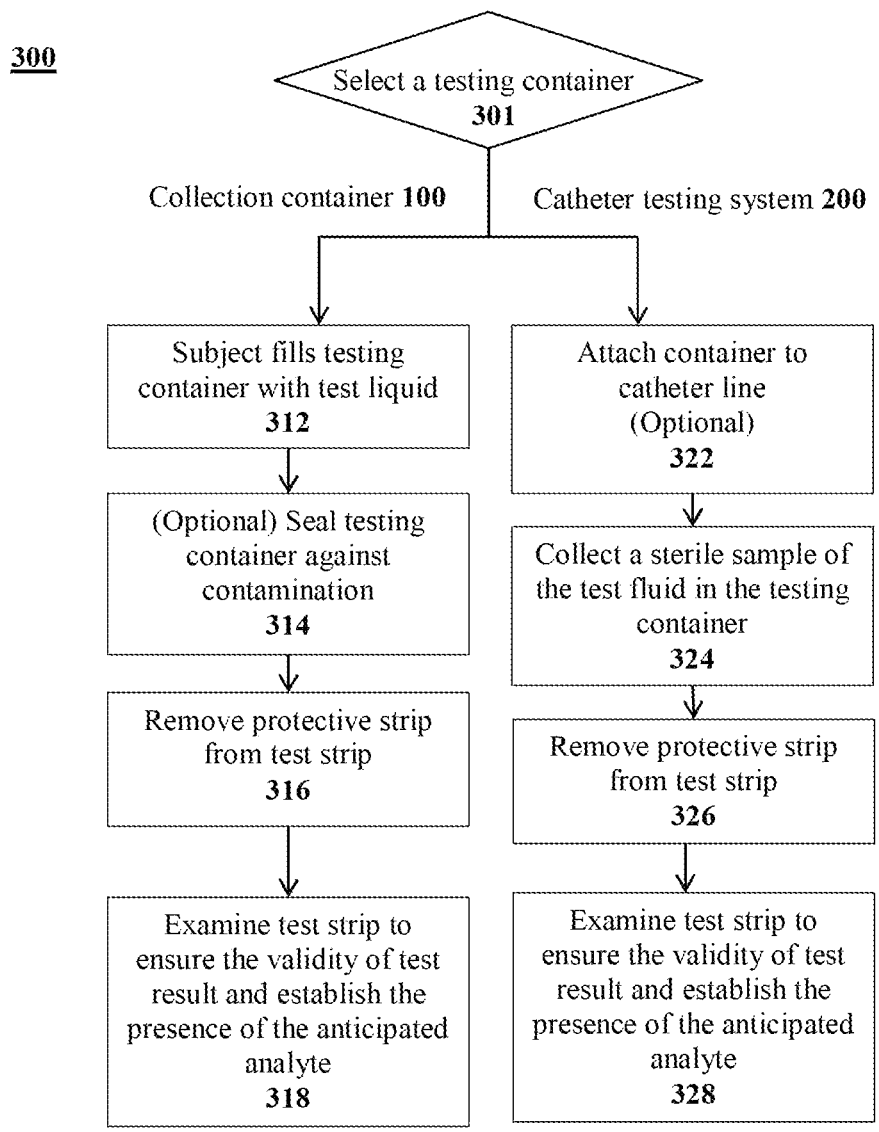
FIG. 3 is a flow diagram depicting a sample collection and assay analysis method according to aspects of the present disclosure.

FIG. 3, with respect to the example test device embodiments disclosed by FIGS. 1 and 2, depicts a flow diagram providing a sample collection and assay analysis the method 300 according to aspects of the present disclosure. As determined by the desired testing circumstance, a user, medical practitioner, or other analyst may select a testing container or system 301 for an anticipated analyte in accordance with the embodiments of the present invention described with respect to FIG. 1, a collection container 100, or with respect to FIG. 2, a catheter testing container is attached in accordance with the catheter testing system 200. According to aspects of the present disclosure, if the collection container 100 is chosen, the user or test subject fills the collection container 100 with the desired biological liquid sample (e.g., urine) as indicated at 312. The user, medical practitioner, or other analyst responsible for analyzing the results of the assay may then optionally seal the test container 100 against further contamination as indicated at 314. Certain embodiments of the present invention described with respect to FIG. 1 allow for the removal or dissolution of the protective strip from contact with the test strip as indicated at 316 when the collection container 100 is in a sealed configuration; other embodiments require that the user or analyst utilize a sterile device or accessory to remove the protective strip from the test strip. The assay is then allowed to develop and provide a visual indicator which indicates the presence or absence of the anticipated analyte as indicated at 318.

According to alternative embodiments of the present disclosure, if the catheter testing system 200 is chosen, the catheter testing container 202 may be attached to a catheter line 204 as indicated at 322. This is optional and not strictly necessary if, the container 202 and catheter line 204 are manufactured as a unit. Certain embodiments of the present invention described with respect to FIG. 2 allow for the removal or dissolution of the protective strip from contact with the test strip as indicated at 324 when the catheter collection system 200 is in a sealed configuration; other embodiments require that a medical practitioner remove the protective strip from the test strip just prior to assembly of the catheter testing system 200 as indicated at 322. The test subject's natural body processes then provide a sample of the test liquid into the catheter testing system as indicated at 326. The order of 324 and 326 may be reversed from that shown in FIG. 3, i.e., the sample may be collected at 326 prior to removing the protective strip from the test strip at 324, in order to collect a sterile sample. The assay is then allowed to develop and provide a visual indicator which indicates the presence or absence of the anticipated analyte as indicated at 328.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A test device comprising:
   a container for a test liquid;
   a test strip affixed to the interior surface of the container, the test strip comprising a reagent for reacting to a preselected analyte;
   a removable protective strip, wherein the protective strip covers a reactive surface of the test strip, wherein a free end of the removable strip extends beyond an opening to the outside of the container, and wherein the opening is a leak-proof seal.

2. The test device of claim 1, wherein the test device is a pregnancy test device.

3. The test device of claim 2, wherein the reagent comprises an antibody reactive to Human Chorionic Gonadotropin (hCG).

4. The test device of claim 3, wherein the antibody is tagged with an indicator for indicating the presence of hCG.

5. The test device of claim 1, wherein the test strip-facing side of the removable protective strip is coated in an adhesive.

6. The test device of claim 1, further comprising a lid configured to seal the container, wherein the test strip is visible from outside the sealed container.

7. The test device of claim 6, wherein the removable strip is removable when the container is sealed by the lid.

8. A method for determining the presence of an analyte in a sample test liquid, comprising:
   collecting the test liquid in the of claim 1, wherein the test strip is protected from exposure to the test liquid and the atmosphere by the removable protective strip;
   removing the removable protective strip through the leak-poof seal by pulling the free end after the test liquid has been collected, thereby allowing a reaction between the reagent and the analyte if present in the test liquid;
   examining the reaction to establish the presence of the analyte.

9. The method of claim 8, further comprising sealing the container after collecting the sample and prior to removing the removable strip in order to prevent sample contamination.

* * * * *